United States Patent [19]

Crew

[11] Patent Number: 4,796,315
[45] Date of Patent: * Jan. 10, 1989

[54] ROTATIONALLY CONTOURED LUMBAR CUSHION

[76] Inventor: Randolph E. Crew, 110 Stonehedge Dr., Greenville, S.C. 29615

[*] Notice: The portion of the term of this patent subsequent to Mar. 10, 2005 has been disclaimed.

[21] Appl. No.: 822,321

[22] Filed: Jan. 27, 1986

[51] Int. Cl.$^4$ .......................... A61F 5/01; A47C 20/02
[52] U.S. Cl. .......................... 5/431; 5/81 R; 5/432; 128/78
[58] Field of Search .................. 5/431, 432, 443, 434, 5/436, 437, 448, 81 R; 128/68, 78; D6/596, 601; 2/44

[56] References Cited

U.S. PATENT DOCUMENTS

| | | | |
|---|---|---|---|
| D. 279,642 | 7/1985 | Ross | D6/596 |
| D. 282,990 | 3/1986 | Sims et al. | D6/596 |
| 2,250,267 | 7/1941 | Lins | 5/431 |
| 2,769,485 | 11/1956 | Shapiro | 5/432 |
| 3,154,072 | 10/1964 | Mack | 128/78 |
| 4,034,748 | 7/1977 | Winner | 5/434 |
| 4,074,373 | 2/1978 | Garofalo | 5/434 |
| 4,431,232 | 2/1984 | Hannouche | 5/432 |
| 4,471,993 | 9/1984 | Watson | 5/432 |
| 4,502,170 | 3/1985 | Morrow | 5/431 |
| 4,572,167 | 2/1986 | Brunswick | 128/78 |

FOREIGN PATENT DOCUMENTS

| | | | |
|---|---|---|---|
| 957440 | 11/1974 | Canada | 5/432 |
| 2016932 | 9/1979 | United Kingdom | 5/434 |
| 1590583 | 6/1981 | United Kingdom | 5/432 |

OTHER PUBLICATIONS

"Posture Curve" Lumbar Support, appearing in a Trade Brochure of "Body Care Inc.", 121 24th St., N.Y., N.Y. 10010.

Primary Examiner—Alexander Grosz

[57] ABSTRACT

A rotationally contoured lumbar cushion (10) is disclosed which may be securely strapped in a lumbar cradling position about the lumbar area of a person. The lumbar cushion cradles the lumbar area of the spine in a sitting position or the supine of bedrest position for prolonged periods of use while sleeping. The lumbar cushion includes a lumbar cradle (A) and a lower base (B). Winged side extensions (C) create rotational sidewalls (40,42) facilitating turning of the person while in bed and securely strapped with the lumbar cradle (20) in place.

8 Claims, 2 Drawing Sheets

4,796,315

ROTATIONALLY CONTOURED LUMBAR CUSHION

BACKGROUND OF THE INVENTION

The invention relates to a lumbar cushion which may be strapped to the lower back of a person for maintaining the spine in its naturally curved position while lying in a supine position, thus allowing the muscles associated with the lumbar area of the spine to relax. In particular, the invention relates to a lumbar cushion adapted to be worn about the lower back of a human while lying on a horizontal bed surface in such a manner that the person can rotate from a supine position to a side rotated fetal position, or from side-to-side fetal positions without altering the lumbar cradling position of the cushion.

Many prior art devices have attempted to provide increased comfort within the lower portion of the back of a person while in a sitting position or in a lying position. Many such devices are described within prior patents.

For example, U.S. Pat. No. 3,765,271 discloses a lumbar support pad having a convex support surface which is contoured to fit the longitudinal curvature of the spine in the lumbar area. A second concave surface is formed to engage the lumbar area laterally across the lower back portion. Further devices of this type have been proposed which have been specially contoured to fit within the lower back portion for supporting the lower back area either while sitting or while lying. The problem occurs that while such a device may offer temporary support to the lumber area, it is not practical to use during prolonged periods of sleep or rest since the person must remain in a supine position which is difficult for prolonged periods of sleep or rest.

In another direction, many prior devices have been subjects of patents which are designed as belts to alleviate discomfort in the lower back portion by strapping a pad or other support against the lumbar area. For example, U.S. Pat. Nos. 2,010,163, 3,052,236, 3,154,072, and 4,475,453 all show belt devices having a pad or other lumbar engaging device. However, these devices fall mainly in the nature of a brace, and do not attempt to function as a cushion or pillow for cradling the lumbar area.

While many backresting lumbar cushions have been available within the prior art, no lumbar cushion has been totally satisfactory for properly cushioning the spine to minimize tension and unnatural curvature during prolonged periods of bedrest and sleeping, allowing versatility of positioning of the person in a number of supine and side rotated fetal positions.

Accordingly, an object of the present invention is to provide a lumbar cushion which may be secured to the body of a person in a lumbar cradling position for maintaining the spine in a naturally curved position while the person is lying in a supine position allowing the muscles associated with the lumbar area of the spine to relax during prolonged periods of bedrest and sleep.

Still another object of the invention is to provide a lumbar cushion which may be worn by a person which allows for rolling to side rotated fetal positions and back to supine positions without disturbing the cradling of the lumbar area by the cushion when in the supine position, or interfering with the comfort of the person in the fetal position.

Another object of the invention is to provide a lumbar cushion which may be secured to the body of a person and provide stability in both side rotated fetal positions and supine positions which is importantly advantageous for an elderly person. The cushion may be secured by a strap and contoured to facilitate turning of the body while cradling the lumbar area.

Another object of the invention is to provide a lumbar cushion which may be strapped about the lumbar area to cradle the lumbar area while sitting, correcting posture and alleviating lower back pain.

A further object of the invention is to provide a lumbar cushion which may be strapped to the lumbar area for use in pregnancy to assist the muscles in supporting the extra weight forward, and to shift the center of gravity rearwards so that stress is relieved from the erector spinae. The same advantages would also apply for an obese person.

SUMMARY OF THE INVENTION

The above objectives are accomplished according to the present invention by providing a rotationally contoured lumbar cushion which may be strapped about the lumbar area. The lumbar cushion includes a convex cradle surface which cradles the spine in the lumbar area longitudinally. The lumbar cushion further includes a concave cradle surface which laterally spans the lumbar area across a substantial portion of the lower back terminating in winged extensions which engage the sides of the lower back. The winged extensions are defined by outwardly tapered walls extending from a lower base outwardly to the upper ridges of the concave cradle surface facilitating rotation of the person when the cushion is strapped about the lumbar area. A fulcrum is provided by the outwardly tapering walls and the lower base about which a person may rotate with the strapped lumbar cushion between a plurality of supine and side rotated fetal positions.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

The invention relates to the cradling and cushioning of the lumbar area of the spine without excessive pressure on the spine in that area, thus allowing the muscles associated with the lumbar area of the spine to relax. For purposes of this disclosure, the term "lumbar area" includes the longitudinal section of the spine extending generally from the sacra to the dorsal section. The lumbar cushion in accordance with the invention is adapted for cradling the lower portion of the back in the lumbar area, and for a considerable extent laterally, on either side of the spine in the lumbar area. A cushion so designed is securely strapped by an adjustable strap encircling the lumbar cushion and the person wearing the cushion, so that the cradling and support effect of the lumbar cushion is maintained during prolonged periods of time of bedrest while the person rotates between side rotated fetal positions and supine positions.

Figure 1:
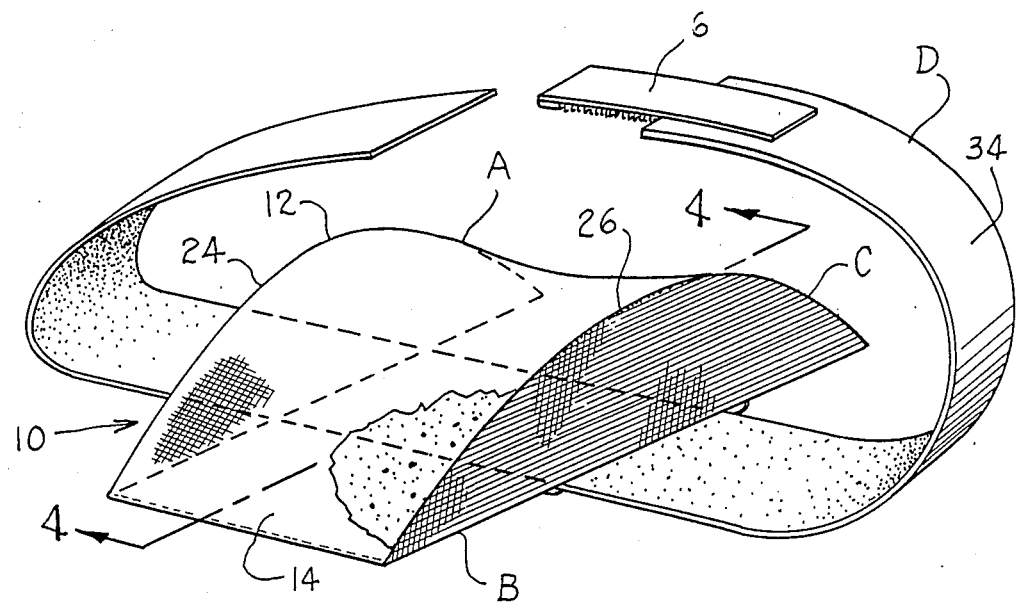
FIG. 1 is a perspective view illustrating a rotationally contoured lumbar cushion constructed in accordance with the present invention.

Referring now in more detail to the drawings, FIG. 1 illustrates a rotationally contoured lumbar cushion, designated generally as 10, constructed in accordance with the present invention which includes a foam cushion block having upper cradle surface A and a lower planar base surface B. A pair of winged sidewall extensions C extend from the lower base B to an upper ridge of the upper cradle A. Strap means D encircles the base B of the cushion and is adapted to be worn about the waist of a person.

The entire lumbar cushion 10 is preferably constructed from a block of treatable polyurethane foam which is washable. The foam material is resilient, yet firm enough to cushion the lumbar area with support. The foam block may be covered with a light cotton cover so that the entire cushion may be machine washed.

Figures 2, 4:
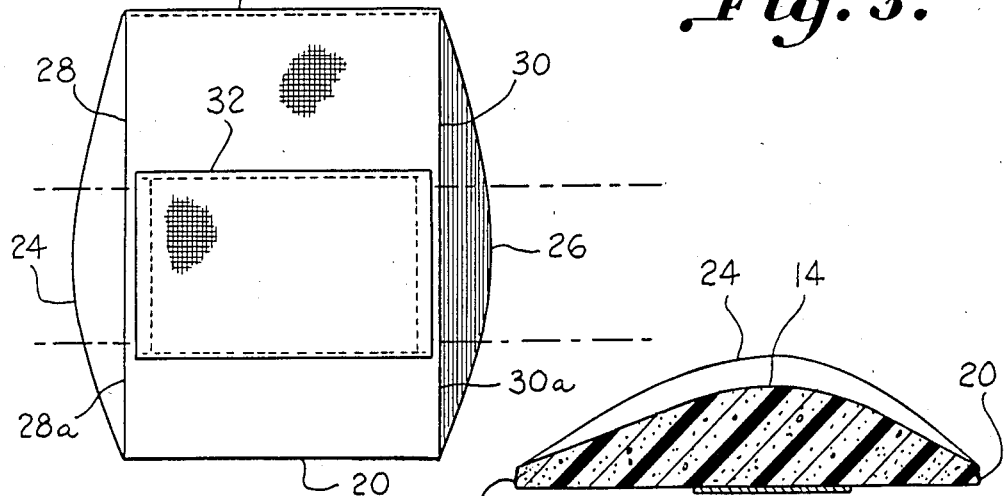
FIG. 2 is a bottom plan view of a rotationally contoured lumbar cushion constructed according to the present invention.
FIG. 4 is a sectional view taken along line 4—4 of FIG. 1.

The lumbar cradle A includes a first convex cradle surface 14 which extends from one end 18 of the cushion block to a second end 20 as can best be seen in FIG. 4. A second concave cradle surface 22 is formed in the lumbar cradle A from one ridge 24 of a winged extension C to an opposing ridge 26 of opposing winged extension C.

Figure 5:
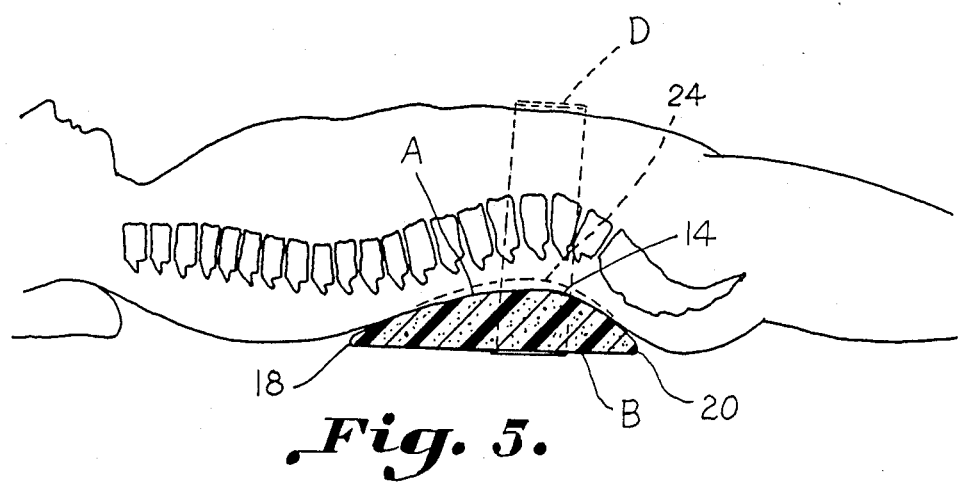
FIG. 5 is a schematic illustration illustrating a person in a supine position cradled by a lumbar cushion according to the present invention.

The lower base B includes a planar base surface having a sufficient lateral extent that it provides a stable base surface for the lumbar cushion and person cradled thereby in a supine position such as shown in FIG. 5. However, it is preferred that the width of the planar base B not be any more than is necessary to provide the desired stability, since one objective of the invention is to provide a lumbar cushion which, when strapped, facilitates rotation of the person between side rotated and supine positions. For this purpose, the dimensions of the lumbar cushion are deemed significant parameters to the proper stable cradling of the lumbar area and turning of the person. As can best be seen in FIG. 2, ridges 24 and 26 of the opposing wing extensions normally will extend laterally ¾ inch to 3 inches and preferably 1½ inches to 1¾ inches at their maximum point of curvature distance from edges 28 and 30 of lower base B respectively.

An open sleeve 32 is affixed to the bottom of lower base B which slideably receives strapping means D which is provided in the form of a 4-inch wide cushion belt 34 having sufficient length to accommodate a wide variety of waist sizes. A 4-inch tab 36 of hook and loop type material, such as the one sold under the trademark of Velcro is provided to fasten to belt 34.

The cushion block is rotationally contoured by each winged extension C extending from side of the cushion block as defined by outwardly tapered rotational sidewalls 40 and 42 which intersect with edges 28 and 30 of the lower base. The person and strapped cushion turn on rotational sidewalls about a fulcrum 28a and 30a defined at the sidewall and base intersection. This enables turning in bed from one side fetal position to another, or from a supine position to a side rotated fetal position with comfort and without disturbing lumbar cradling provided when in the supine position. The winged extensions C are further defined by lateral extension 22a and 22b of the concave cradle surface 22 extending beyond respective edges 28 and 30 of the lower base. In practice, the angular inclination of the rotational sidewalls 40 and 42 is found to be a significant parameter. Although any angle between 45 degrees and 75 degrees may be used in a given situation, a prescribed 60 degree angle between sidewalls 40, 42 and the lower base is desired.

Figure 3:
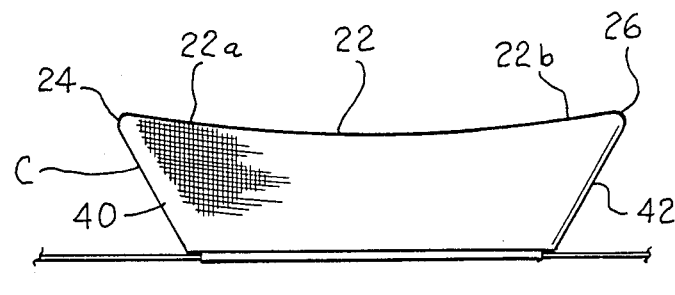
FIG. 3 is an end view of a rotationally contoured lumbar cushion constructed according to the present invention.

Concave surface 22 determines the lateral cradling effect of the cushion. It begins at the peak of ridge 24 and curves to the peak of ridge 26 as best illustrated in FIG. 3. The width of lower base B, the angular inclination of the rotational sidewalls 40 and 42, and the curvature of contoured surface 14 will all determine the radius of curvature of this surface. Although concave surface 22 may curve to a point from 1 inch to 3½ inches above lower base B to 2 inches to 5 inches at outer ridges 24 and 26, a depth of 2⅝ inches above lower base B to 3 inches at outer ridges 24 and 26 is desired. In this case, the other dimensions of the cushion include a lower base B of 9 inches wide and 12½ inches long, with sidewalls 40 and 42 cut at a 60 degree angle and extending 1½ inches from edges 28 and 30. The result will be a desired radius of curvature for concave surface 22 of 37⅞ inches.

Contoured surface 14 determines the longitudinal cradling effect of the cushion, beginning at cushion end 18 and ending at cushion end 20. Although the straight line distance from end 18 to end 20 may vary from 10 to 16 inches, it is generally desirable to make the cushion 12½ inches long. Contoured surface 14 may therefore peak at between 1 and 3½ inches, but preferably a peak, or leveling off, at 2½ to 2⅝ inches is desired. This peak should occur approximately 5½ to 6 inches from cushion end 20 so as to correspond to the natural human spinal arch at the third and fourth vertebrae. The radius of curve of this peak, or arch, in contoured surface 14 will again be determined by the other dimensions, but for a cushion 9 inches by 12½ inches with sidewalls cut at a 60 degree angle, and ridges 24 and 26 being 3 inches above lower base B, the radius of curvature for contoured surface 14 will be 5½ inches at the peak. After curving for approximately 52 degrees of arc, the curve of surface 14 flattens and continues on a tangent to cushion ends 18 and 20 respectively. Also under the above cushion parameters, outer ridges 24 and 26 have a radius of curvature of 4½ inches for approximately 60 degrees of arc before flattening and continuing on a tangent to cushion ends 18 and 20 respectively.

In accordance with the method of the instant invention, a lumbar cushion adapted to be worn about the lumbar area is provided which may be securely strapped about the waist of a person. The lumbar cushion is provided by contouring, in a resilient polyurethane cushion block, a double-contoured surface which includes longitudinally convex surface 14 and lateral concave surface 22. The lateral concave surface is provided with winged lateral extensions C which create rotationally contoured sidewalls 40 and 42 that facilitate turning of the lumbar cushion when securely strapped about the lumbar area and waist of the person. While spanning a sufficient extent of the width of the lower back, the winged extension C firmly grip the sides of the lower back adjacent the lumbar area when it is securely strapped thereto. Turning is facilitated without disturbing the cradling position of the lumbar cushion. In this manner, the lumbar cushion cradles the lumbar area along a significant longitudinal portion and side-to-side, keeping the natural curve of the spine when lying on the back, and dissipating the weight to a substantial cushion area. The muscles surrounding the spine in the lumbar area relax naturally when the natural curve is established in the supine position only; the back is flat in the fetal position. The strap D preferably is ¼ inch foam which is sufficiently thick to allow a cushion effect as the waist area expands with body movement, and which is sufficiently wide, preferably 4 inches, as not to cause binding.

Figure 6:
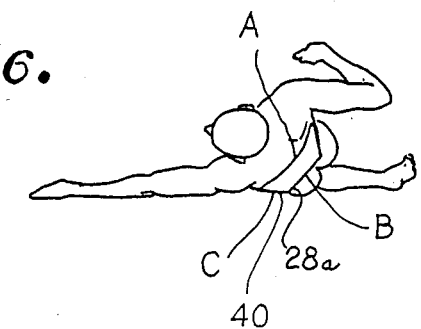
FIG. 6 is a schematic illustration illustrating a person wearing a lumbar cushion constructed according to the present invention, turning from a side rotated fetal position to a supine position, or vice versa.
Figure 7:
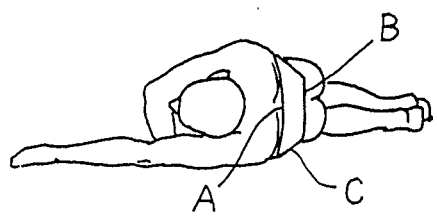
FIG. 7 is a schematic illustration illustrating a person wearing a lumbar cushion according to the invention in a side rotated fetal position.
Figure 8:
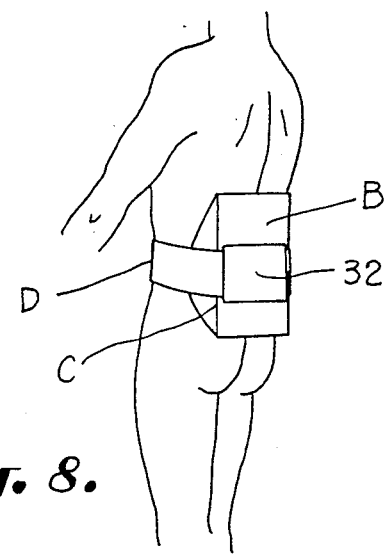
FIG. 8 is a schematic view illustration a person standing with a lumbar cushion according to the invention securely strapped about the lumbar area.

Referring now to FIGS. 7–8, use of a lumbar cushion constructed in accordance with the invention will be described. In FIG. 5 a person is illustrated with lumbar cushion 10 cradling the lumbar area of the person as strapped around the waist. It can be seen that convex surface 14 follows the natural contour of the spine with ridges 24, 25 of winged extension C of the higher ridge 24 comfortably wrapped around the lower back laterally about the spine in the lumbar area. The double contour dissipates pressure at the spine and the spine is supported without undue pressure. As can be seen in FIG. 6, should the person begin to turn to a side rotated fetal position, the strapped cushion block rotates with the person about the rotationally contoured sidewalls 40 and fulcrum 28a which facilitates natural turning to the side position as can be seen in FIG. 7. FIG. 8 illustrates the lumbar cushion securely strapped in a lumbar cradling position about the waist of a person. The lightweight polyurethane cushion block may be worn all day by the person, if desired, to provide support in a sitting position or lying position as the person may assume.

Thus, it can be seen that an advantageous construction can be had according to the invention for a rotationally contoured lumbar cushion which may be securely strapped in a lumbar cradling position and worn while sitting or lying. When lying in bed, the strapped and contoured lumbar cushion facilitates rotating and turning between side rotated fetal positions and supine positions. The spine in the lumbar areas is cradled in the supine position and afforded support which allows muscles in the lumbar area to relax and the lower spine to assume its natural lordotic curve. The cushion allows the back to naturally flatten in the fetal position, thus allowing the lower spine to go from flat in the fetal position to a natural lordotic curve in the supine position as the person changes positions during sleep. This flexing of the lower spine during prolonged periods of sleep, plus establishing the naturally relaxing lordotic curve in the supine position, allows the person to wake up more flexible and relaxed, thus avoiding the morning "stiff back." The act of supporting the lumbar area of the spine and relaxing the associated muscles has also proven to be useful in treating a variety of low back problems including pulls, sprains and spasms.

While a preferred embodiment of the invention has been described using specific terms, such description is for illustrative purposes only, and it is to be understood that changes and variations may be made without departing from the spirit or scope of the following claims.

What is claimed is:

1. A rotationally contoured lumbar cushion for cradling the lumbar area while strapped to the back and facilitating turning while lying in a variety of bedrest positions comprising:

a cushion block of resilient polyurethane foam material having a lower base and an upper lumbar cradle;

said upper lumbar cradle including a convex surface for engaging a length of the spine along said lumbar area;

a concave cradle surface formed in said lumbar cradle spanning the lumbar area laterally from adjacent one side of the back to the other;

a winged cradle extension defined by said concave cradle surface extending past said lower base on opposing sides of said lower base for gripping the sides of said back, spanning said lumbar area laterally;

a rotationally contoured sidewall tapering outwardly from each said opposing side of said lower base to said winged cradle extension at each side of said cushion block, the sidewalls defining defining angles between said sidewalls and the lower base of between 45° and 75°;

said rotationally contoured sidewalls defining a fulcrum at the intersection of said lower base facilitating turning of said cushion block cradling said lumbar area between side rotated fetal and supine positions; said outwardly tapered sidewall and said lower base about which said cushion block rotates;

strap means encircling said cushion block and a waist of said person for strapping said cushion block in a lumbar cradling position during turning; and said strap means securing said lateral winged cradle surfaces against side portions of the lower back of said person to facilitate rotation of said person without altering the cradling position of said cushion block while supporting the spine in said lumbar area.

2. The device of claim 1 wherein said cushion block base includes a planar base surface which has a sufficient width to provide a stable base surface yet allows rotation of the body of said person from either a side-to-side position or a back-to-side position with comfort while said cushion block is strapped in said lumbar cradling position.

3. The device of claim 1 wherein said winged cradle extensions terminate in raised ridges which wrap around opposing back sides of said person when worn in a lumbar cradle position thereby gripping said backsides when supporting a person in a supine position and rotating therefrom from side to side.

4. The device of claim 1 wherein said strap means is slideably affixed to said lower base of said cushion block.

5. The lumbar cushion of claim 1 wherein said concave cradle surface has a radius of curvature of approximately 37⅝ inches and a span of approximately 12½ inches.

6. The lumbar cushion of claim 1 wherein said convex surface has a radius peak at approximately 2/5 of the distance from one end of said cushion block which has a radius of curvature of approximately 5½ inches.

7. The lumbar cushion of claim 1 wherein said concave surface has a low point from 1 inch to 3½ inches above said lower base and a high point at the outer edges of said concave surface of approximately 2 inches to 5 inches.

8. The lumbar cushion of claim 1 wherein said strap means includes a length of belting and fastening means in the form of hook and loop type material of sufficient length to adjust said strap means tightly about the waist of the majority of people.

* * * * *